(12) United States Patent
Di Censo et al.

(10) Patent No.: US 9,942,647 B2
(45) Date of Patent: Apr. 10, 2018

(54) HEADPHONES WITH THERMAL CONTROL

(71) Applicant: HARMAN INTERNATIONAL INDUSTRIES, INC., Stamford, CT (US)

(72) Inventors: Davide Di Censo, Oakland, CA (US); Stefan Marti, Oakland, CA (US); Jaime Elliot Nahman, Oakland, CA (US)

(73) Assignee: HARMAN INTERNATIONAL INDUSTRIES, INCORORATED, Stamford, CT (US)

( * ) Notice: Subject to any disclaimer, the term of this patent is extended or adjusted under 35 U.S.C. 154(b) by 62 days.

(21) Appl. No.: 14/874,236

(22) Filed: Oct. 2, 2015

(65) Prior Publication Data
US 2017/0099539 A1   Apr. 6, 2017

(51) Int. Cl.
| | |
|---|---|
| *H04R 1/10* | (2006.01) |
| *G05D 23/00* | (2006.01) |
| *A61B 5/01* | (2006.01) |
| *A61B 5/00* | (2006.01) |

(52) U.S. Cl.
CPC ........... *H04R 1/1091* (2013.01); *G05D 23/00* (2013.01); *H04R 1/1008* (2013.01); *A61B 5/01* (2013.01); *A61B 5/6803* (2013.01); *H04R 1/1041* (2013.01); *H04R 2201/10* (2013.01); *H04R 2430/00* (2013.01)

(58) Field of Classification Search
CPC ...... H04R 29/001; H04R 3/007; H04R 5/033; H04R 5/04; H04R 1/1041; H04R 3/02; H04R 3/08; H04N 21/812; H04N 21/4325; H04N 21/438; H04N 21/44016; H04N 21/458; H04N 21/6587; H04N 5/76; H04N 9/79; H04N 21/235
USPC ...... 381/74, 150, 182, 370, 374, 1, 379, 309
See application file for complete search history.

(56) References Cited

U.S. PATENT DOCUMENTS

| | | | |
|---|---|---|---|
| 6,788,797 B2 | 9/2004 | Kim | |
| 8,397,518 B1 * | 3/2013 | Vistakula | ................ F25B 21/02 |
| | | | 62/259.3 |
| 2008/0025525 A1 * | 1/2008 | Tsai | ..................... H03G 3/3005 |
| | | | 381/74 |

(Continued)

FOREIGN PATENT DOCUMENTS

| | | | | |
|---|---|---|---|---|
| CN | 101494811 A | | 7/2009 | |
| EP | 2851001 A2 | | 3/2015 | |
| JP | 2012191363 | * | 10/2012 | ............... H04R 1/10 |

OTHER PUBLICATIONS

The Wireless Headphone Ear Warmers, http://www.hammacher.com/Product/84203.

(Continued)

*Primary Examiner* — Lun-See Lao
(74) *Attorney, Agent, or Firm* — Artegis Law Group, LLP

(57) ABSTRACT

The various embodiments set forth a headphone apparatus that includes a first earcup, a sensor included in the first earcup, and a controller. The first earcup is coupled to a headband, and includes a loudspeaker system and a thermal control subsystem. The controller is configured to detect an output generated by the sensor, and, based on the output, transmit a signal to the thermal control subsystem included in the first earcup to modify a temperature associated with at least the first earcup.

20 Claims, 10 Drawing Sheets

(56) References Cited

U.S. PATENT DOCUMENTS

| | | | | |
|---|---|---|---|---|
| 2009/0097689 A1* | 4/2009 | Prest | ............... | H04R 1/028 |
| | | | | 381/380 |
| 2010/0195851 A1* | 8/2010 | Buccafusca | ............ | H04R 17/02 |
| | | | | 381/190 |
| 2011/0268290 A1 | 11/2011 | Lee | | |
| 2012/0194343 A1 | 8/2012 | Livingston | | |
| 2013/0243235 A1* | 9/2013 | Clayton | ............... | H04R 1/1008 |
| | | | | 381/371 |

OTHER PUBLICATIONS

Thermoelectric cooling, http://en.wikipedia.org/wiki/Thermoelectric_cooling.

Extended European Search Report for Application No. 16188986.0 dated Feb. 9, 2017.

* cited by examiner

HEADPHONES WITH THERMAL CONTROL

BACKGROUND

Field of the Various Embodiments

The various embodiments relate generally to headphone technology and, more specifically, to headphones with thermal control.

Description of the Related Art

Around-the-ear, or circumaural, headphones that completely surround the ears are commonly employed by music professionals, such as front-of-house mixers, sound engineers, and musicians, among others. Supra-aural headphones, which rest directly on the user's outer ear, are also frequently used, for example in conjunction with portable music players and the like. As the use of such headphones in everyday life becomes increasingly common, both circumaural and supra-aural headphones are being worn by more users and for longer periods of time.

One common problem oftentimes experienced by users is that wearing headphones for extended periods can cause the user's ears to heat up and create a need to remove the headphones due to the discomfort and distraction oftentimes associated with such heating. Furthermore, both supra-aural and circumaural headphones generally interfere with and/or prevent the wear of most ear-insulating apparel and many types of head-insulating apparel. Thus, in colder climates and in overly air-conditioned buildings, the ears of users of headphones may get cold while wearing these types of headphones.

As the foregoing illustrates, headphone designs that enable users to more comfortably wear these types of headphones in a variety of environmental conditions would be useful.

SUMMARY

The various embodiments set forth a headphone apparatus that includes a first earcup, a sensor included in the first earcup, and a controller. The first earcup is coupled to a headband, and includes a loudspeaker system and a thermal control subsystem. The controller is configured to detect an output generated by the sensor, and, based on the output, transmit a signal to the thermal control subsystem included in the first earcup to modify a temperature associated with at least the first earcup.

At least one advantage of the various embodiments is that the designs allow headphone users to more comfortably wear headphones in many different environmental conditions and tier longer periods of time without experiencing the thermal discomfort oftentimes associated with conventional headphone designs.

BRIEF DESCRIPTION OF THE SEVERAL VIEWS OF THE DRAWINGS

So that the manner in which the above recited features of the various embodiments can be understood in detail, a more particular description of the various embodiments, briefly summarized above, may be had by reference to embodiments, some of which are illustrated in the appended drawings. It is to be noted, however, that the appended drawings illustrate only typical embodiments and are therefore not to be considered limiting of scope, for the various embodiments may admit to other equally effective embodiments.

For clarity, identical reference numbers have been used, where applicable, to designate identical elements that are common between figures. It is contemplated that features of one embodiment may be incorporated in other embodiments without further recitation.

DETAILED DESCRIPTION

Figure 1:
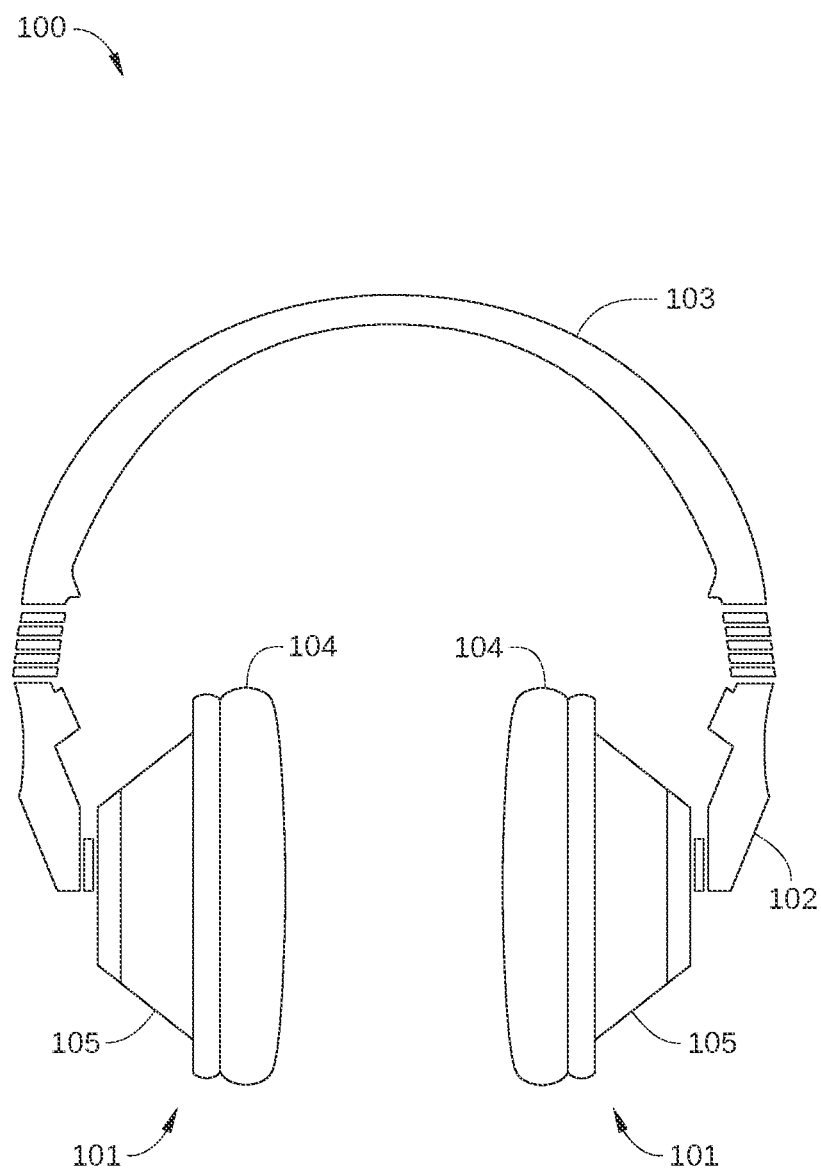
FIG. 1 is a schematic diagram illustrating a headphone system configured to implement one or more aspects of the various embodiments.

FIG. 1 is a schematic diagram illustrating a headphone system 100 configured to implement one or more aspects of the various embodiments. Headphone system 100 may include, without limitation, two earcups 101, coupled to a headband 103 via a respective arm 102. Each earcup 101 is configured to fit over the outer ear of a user, when headphone system 100 is worn by the user, and includes, among other things, an ear-surround cushion 104 coupled to a housing 105. In some embodiments, headphone system 100 may be configured with a single earcup. Furthermore, in some embodiments, headphone system 100 may be configured as a supra-aural headphone system, while in other embodiments, headphone system 100 may be configured as a circumaural headphone system. One embodiment of earcup 101 is illustrated in FIG. 2, in which headphone system 100 is configured as a circumaural headphone system.

Figure 2:
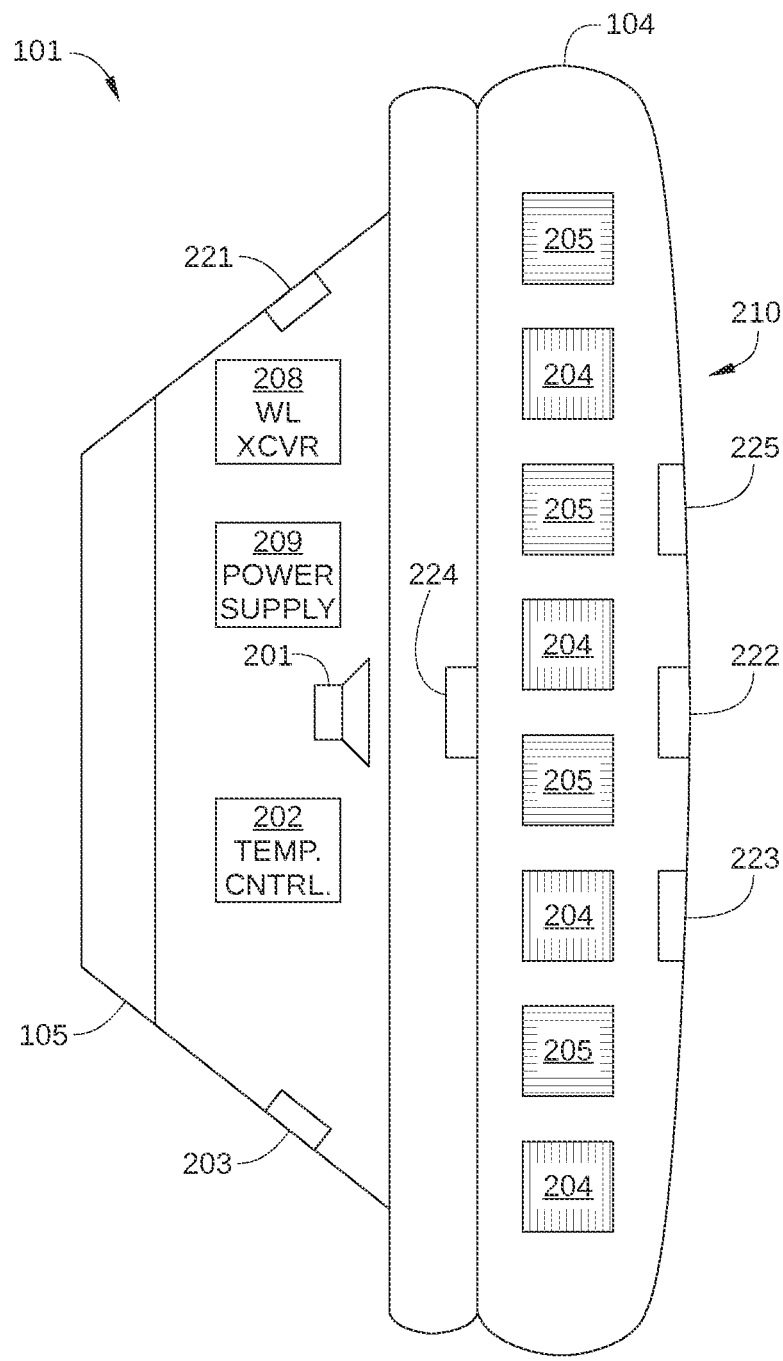
FIG. 2 is a more detailed illustration of the earcup of FIG. 1, according to the various embodiments.

FIG. 2 is a more detailed illustration of an earcup 101 of headphone system 100, according to the various embodiments. As shown, in addition to ear-surround cushion 104 and housing 105, earcup 101 includes, without limitation, a loudspeaker system 201, a temperature controller 202, a user interface 203, one or more heating elements 204, one or more cooling elements 205. In some embodiments, earcup 101 may also include, without limitation, a wireless transceiver 208, such as a Bluetooth® transceiver, a WiFi transceiver, or a wireless Internet transceiver, and/or an internal power supply 209, such as a battery. In addition, headphone system 100 may include, without limitation, one or more sensors, such as an external temperature sensor 221, a user head temperature sensor 222, a galvanic skin response sensor 223, an acoustic cavity temperature sensor 224, a pulse/respiration sensor 225, and the like.

When headphone system 100 is worn by a user, ear-surround cushion 104 seals against the user's head, so that each earcup 101 forms an acoustic cavity 210 around one of the user's ears. By design, ear-surround cushion 104 forms and acoustically isolates acoustic cavity 210 from the surroundings for enhanced listening. The acoustically isolating material of ear-surround cushion 104 generally acts as thermal insulation, while the seal formed by ear-surround cushion 104 inhibits most or all air flow into and out of acoustic cavity 210. Consequently, without the thermal control provided by temperature controller 202 and associated temperature control elements of headphone system 100, when headphone system 100 is worn for an extended period, overheating of the user's ears and portions of the user's head in contact with acoustic cavity 210 may result. Acoustic cavity 210 is shown more clearly in FIG. 3.

Figure 3:
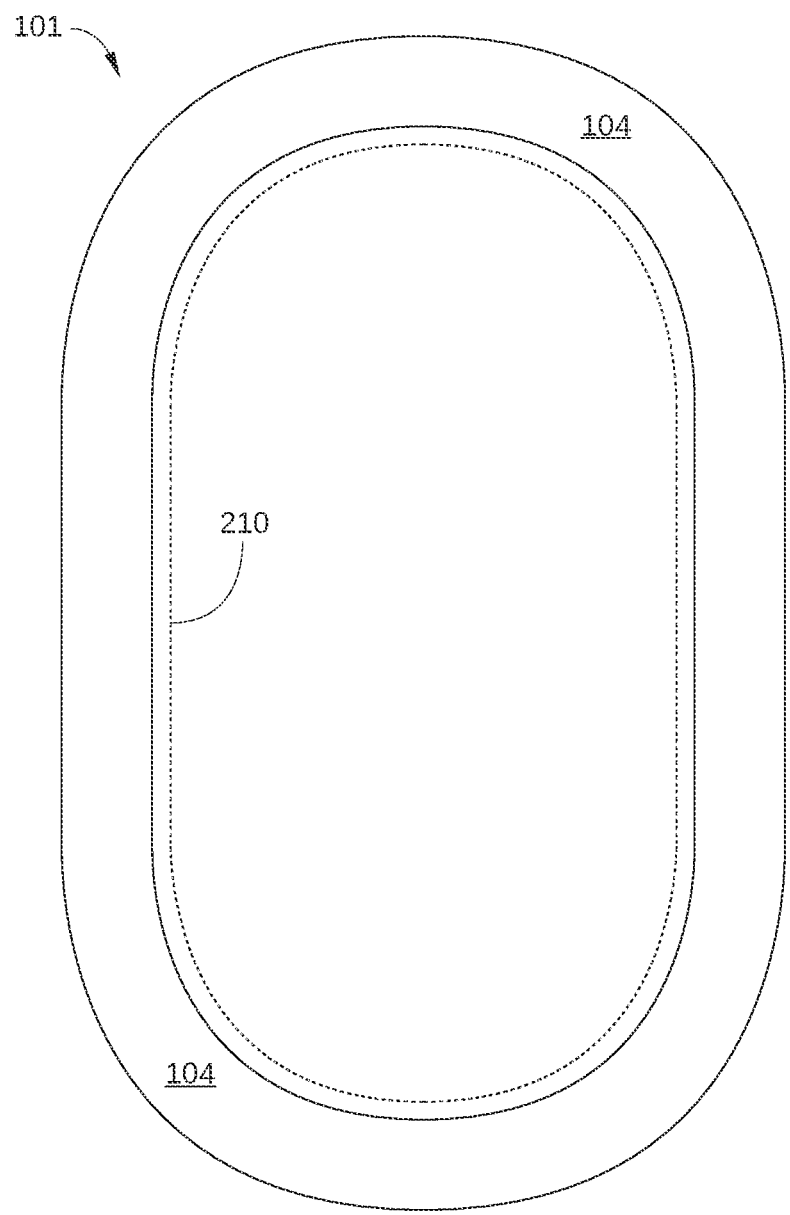
FIG. 3 illustrates a plan view of the acoustic cavity of the earcup of FIG. 2, configured according to the various embodiments.

FIG. 3 illustrates a plan view of the acoustic cavity of the earcup of FIG. 1, configured according to the various embodiments. As shown, acoustic cavity 210 is disposed within the confines of ear-surround cushion 104, so that a user's outer ear (not shown) is contained within acoustic cavity 210. It is noted that in embodiments in which headphone system 100 is configured as a supra-aural headphone system, acoustic cavity 210 is not present.

Returning to FIG. 2, loudspeaker system 201 may be any technically feasible sound-generating system suitable for implementation in a headphone system. Wireless transceiver 208 may provide wireless connectivity to external devices and/or networks. For example, wireless transceiver 208 may enable connectivity to smartphones, electronic tablets, laptop computers, and the like, for additional computational resources and information, and/or connectivity to wireless networks for auxiliary information, such as that available via the Internet. Internal power supply 209 may include, without limitation, any battery and/or miniaturized power generation device suitable for use in headphone system 100. Temperature controller 202 may be any hardware, firmware, or software construct, or any combinations thereof, configured to receive inputs from sensors associated with headphone system 100, determine outputs based on the received inputs, and send the outputs to the appropriate temperature control elements of headphone system 100, (e.g., heating elements 204 and cooling elements 205). Typically, only one of earcups 101 includes temperature controller 202, but in some embodiments, a temperature controller 202 is disposed within each earcup 101.

User interface 203 enables user inputs to temperature controller 202, such as selecting a particular thermal control mode of operation and/or temperature setpoint. Thus, user interface 203 may include, without limitation, one or more mechanical (rocker, up-down, toggle) buttons or touch sensors disposed on an outer surface of housing 105. In some embodiments, user interface 203 may also include, without limitation, one or more display elements configured to provide a visual indicator of the current thermal control mode and/or cooling/heating state of headphone system 100. To that end, user interface 203 may include any combination of display elements suitable for use in headphone system 100, such as a seven-segment liquid crystal (LCD) or light-emitting diode (LED) display, an LCD screen, an e-ink or organic LED display, or one or more appropriately colored LEDs. For example a red LED on one or both of earcups 101 may indicate that headphone system 100 is in heating mode, while a blue LED on one or both of earcups 101 may indicate that headphone system 100 is in cooling mode. Alternatively or additionally, one or more display elements may indicate in what particular thermal control mode headphone system 100 is, such as external condition mode, thermal transparency (internal condition) mode, target setpoint mode, user body condition mode, and temporal mode, among others. Embodiments of the various thermal control modes of headphone system 100 are described below in conjunction with FIGS. 5-7. Alternatively or additionally, the user interface may be part of an application executing on a mobile device (for example, and without limitation, a smartphone or tablet device) or an application executing on a wearable device (for example, and without limitation, a smartwatch, smart-glasses, or a head mounted display device). In some embodiments, a visual indicator of the current thermal control mode and/or cooling/heating state of headphone system 100 may be displayed on a display screen associated with a mobile device or a wearable device via the user interface. The visual indicator may be for example and without limitation, a graphical display element or graphical display icon included within the user interface. Furthermore, in some embodiments, input buttons and other control buttons may be displayed on the screen associated with a mobile device or a wearable device via the user interface for controlling the headphone system 100. The input buttons and other control buttons may be, for example and without limitation, graphical display elements or graphical display icons included in the user interface.

Heating elements 204 may be any technically feasible heating element or apparatus suitable for implementation in headphone system 100, and may be integrated into ear-surround cushion 104 and/or a surface of housing 105 adjacent or proximate to acoustic cavity 210. Heating elements 204 may include, without limitation, electric resistance heating devices and/or heat exchangers, such as liquid-heated elements that receive liquid heated in a remote module. One embodiment of such a remote module is described below in conjunction with FIG. 4.

Cooling elements 205 may be any technically feasible cooling element or apparatus suitable for implementation in headphone system 100, and may be integrated into ear-surround cushion 104 and/or a surface of housing 105 adjacent or proximate to acoustic cavity 210. Cooling elements 205 may include, without limitation, one or more Peltier coolers and/or heat exchangers, such as liquid-cooled elements that receive liquid cooled in the above-described remote module.

External temperature sensor 221 may be any technically feasible sensor configured to measure air temperature outside earcup 101. User head temperature sensor 222 may be any technically feasible sensor configured to measure the temperature of the portion of a user's head that is in contact with ear-surround cushion 104. Alternatively or additionally, head temperature sensor 222 may include a user ear temperature sensor that is specifically configured to contact and measure the temperature of a user's outer ear as a distinct temperature measurement. Galvanic skin response sensor 223 may be any technically feasible sensor configured to measure galvanic response, and therefore sweatiness (or perspiration or diaphoresis), of the portion of a user's head that is in contact with ear-surround cushion 104. Acoustic cavity temperature sensor 224 may be any technically feasible sensor configured to measure air temperature inside earcup 101, i.e., the temperature inside acoustic cavity 210. Pulse/respiration sensor 225 may be any technically feasible sensor configured to detect pulse rate and/or respiration rate of the user, such as a pressure sensor, a sound transducer, or an imager.

Figure 4:
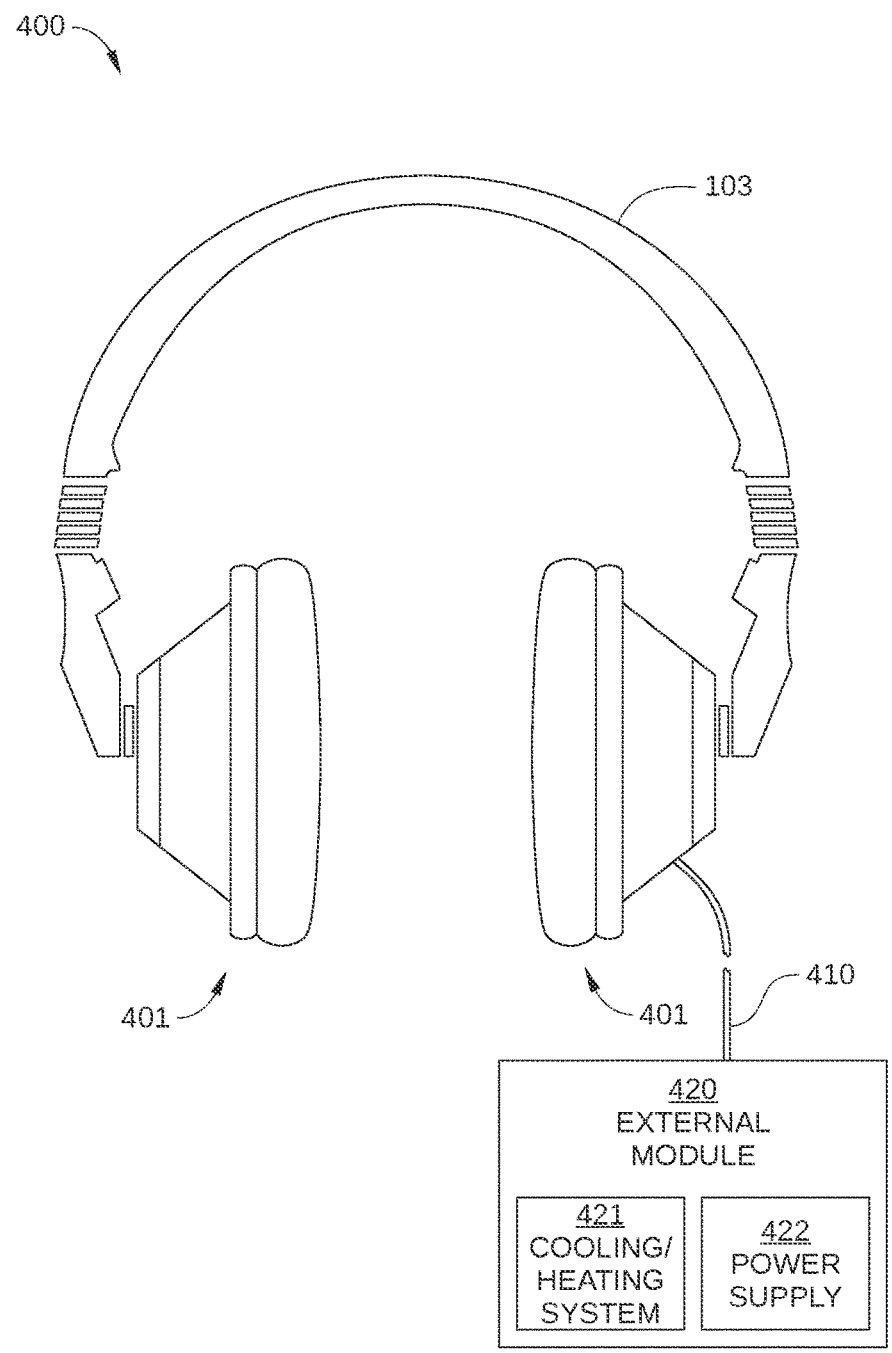
FIG. 4 is a schematic diagram illustrating the headphone system of FIG. 1 configured with an external module, according to the various embodiments.

In the embodiment illustrated in FIG. 2, headphone system 100 is depicted as a cordless system that includes no wired connections or tethers, for freedom of movement and comfort. In other embodiments, a headphone system may include, without limitation, an external module for providing additional capabilities or capacity. One such embodiment is illustrated in FIG. 4. FIG. 4 is a schematic diagram illustrating a headphone system 400 that includes an external module 420, configured according to various embodiments. As shown, headphone system 400 is coupled to external module 420 via a cord 410. External module 420 includes, without limitation, a cooling/heating system 421 and/or a power supply 422.

Cooling/heating system 421 may be any technically feasible liquid cooling and/or heating system, such as a miniaturized refrigeration system (or heat pump system) that cools water and pumps the cooled water to cooling element 205 in earcups 401. In embodiments in which external module 420 includes cooling/heating system 421, cord 410 is configured with a pipe (not shown), flexible or otherwise, for conducting cooled (or heated) liquid to earcups 401. In such embodiments, cooling and heating of the liquid may be used in conjunction with heating elements 204 and cooling elements 205 in FIG. 2. In some embodiments, as shown in FIG. 4, cord 410 may be coupled to only one of earcups 401, in which case the pipe is routed to the second earcup 401 through headband 403. In other embodiments, cord 410 may be directly coupled to both of earcups 401. In embodiments in which external module 420 includes power supply 422, cord 410 is configured with wiring (not shown) configured for powering heating elements 204 and/or cooling elements 205. In some embodiments, cord 410 may be integrated with a cord used to provide signals to loudspeakers in earcups 401.

In the embodiment illustrated in FIG. 2, heating elements 204 are depicted as conductive heating elements integrated into ear-surround cushion 104. In other embodiments, heating elements 204 may include, without limitation, heating elements implemented in conjunction with one or more fans configured to provide convective heat transfer into and/or out of acoustic cavity 210. One such embodiment is illustrated in FIG. 5.

Figure 5:
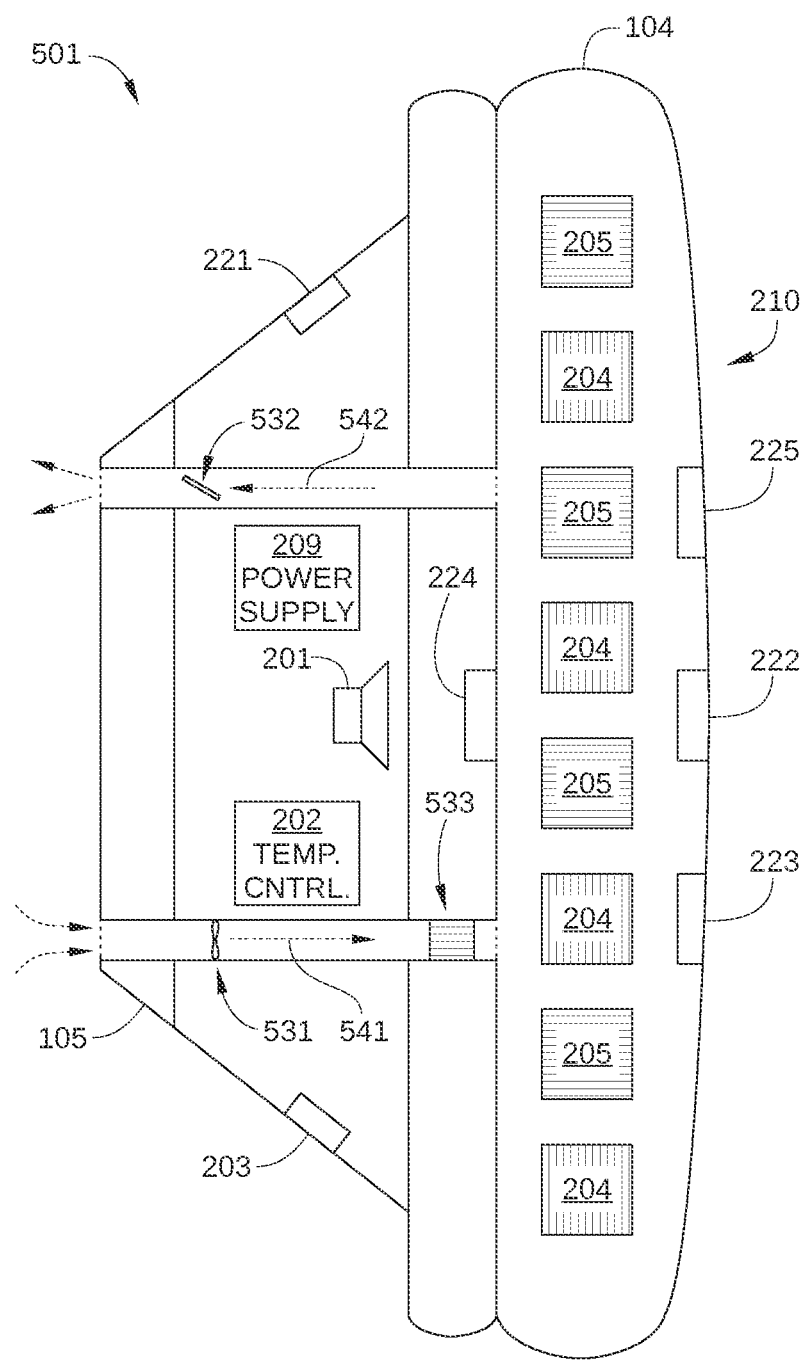
FIG. 5 is a more detailed illustration of the earcup of FIG. 1, according to various other embodiments.

FIG. 5 is a more detailed illustration of an earcup 501 of headphone system 100, according to the various other embodiments. Earcup 501 may be substantially similar in configuration to earcup 101 in FIG. 1, and may also include, without limitation, a fan 531, a damper 532 or other air valve, and/or a heat exchanger 533.

Fan 531 may be any low-noise or ultra-silent fan suitable for use in headphone system 101. In some embodiments, earcup 501 may include active noise cancellation to reduce the impact of fan 531 on the listening experience of the user. Fan 531 may be controlled by temperature controller 202, and is configured to force supply air 541 into acoustic cavity 210 and to cause exhaust air 542 to exit acoustic cavity 210. Supply air 541 is drawn from outside housing 105 as shown, and exhaust air exits acoustic cavity 210, for example via damper 532. The convective heat transfer that results may assist in cooling acoustic cavity 210 when acoustic cavity 210 and/or a portion of the user's head that is in contact with earcup 501 and/or acoustic cavity 210 is overheated.

Damper 532 may be any motorized damper or air valve suitable for use in headphone system 101. Damper 532 is configured to open in response to control signals from temperature controller 202. In some embodiments, damper 532 may be configured to open to allow airflow through acoustic cavity 210 without the additional impetus provided by fan 531. In such embodiments, earcup 501 may include multiple dampers 532 to facilitate sufficient free convection of air through acoustic cavity 210. In other embodiments, damper 532 may be configured to control the flow of supply air 541 and exhaust air 542 by opening or closing, as controlled by temperature controller 202. In yet other embodiments, damper 532 is configured to acoustically seal earcup 501 when fan 531 is not operating. In such embodiments, damper 532 may only be an open-shut air valve and not a flow control valve, and the flow rate of supply air 541 and exhaust air 542 may be controlled by a variable speed motor associated with fan 531.

Heat exchanger 533 may be any heat exchange device configured to heat and/or cool supply air 541. Heat exchanger 533 may be substantially similar to heating elements 204, cooling elements 205, or a combination of both. For example, heat exchanger 533 may include, without limitation, a liquid-to-air heat exchange coil through which cooled and/or heated liquid is pumped. Alternatively, in some embodiments, headphone system 500 does not include heat exchanger 533. In such embodiments, heating is therefore provided by heating elements 204, and cooling by cooling elements 205 and/or supply air 541.

Figure 6:
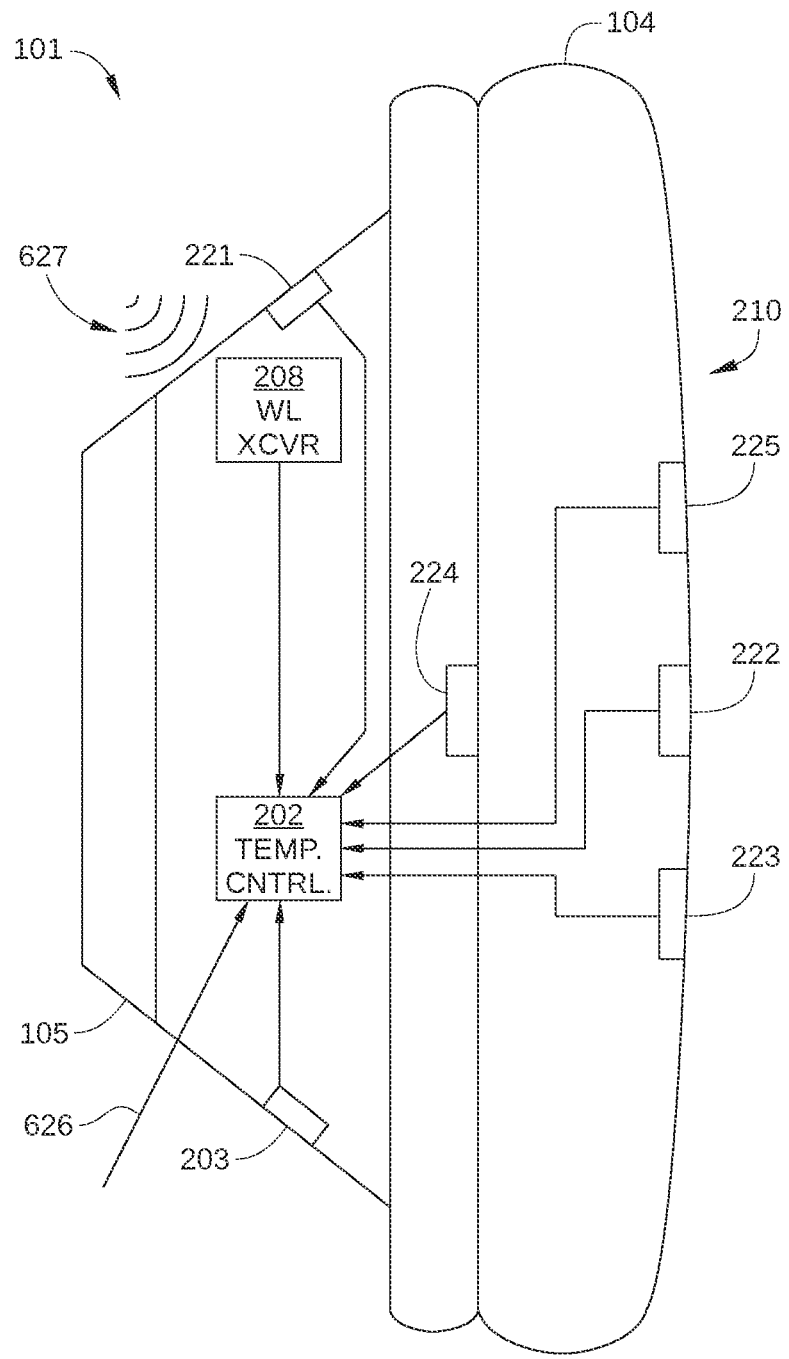
FIG. 6 schematically illustrates an earcup of the headphone system of FIG. 1, as a temperature controller receives sensor inputs, configured according to various embodiments.

According to some embodiments, temperature controller 202 controls a temperature associated with earcup 101 and/or a user (such as a user ear temperature or user head temperature) based on one or more sensor inputs. One such embodiment is illustrated in FIG. 6. FIG. 6 schematic illustrates earcup 101 of headphone system 100 as temperature controller 202 receives sensor inputs, configured according to various embodiments. As shown, temperature controller 202 may receive sensor inputs from one or multiple sensors, including, without limitation, external temperature sensor 221, user head temperature sensor 222, galvanic skin response sensor 223, acoustic cavity temperature sensor 224, pulse/respiration sensor 225, and the like. Alternatively or additionally, temperature controller 202 may receive other inputs 626 from sensors, such as, and without limitation, worn body sensors or other technically feasible sensors, and/or wireless network inputs 627. Wireless network inputs 227 may be received from one or more wireless computing devices, such as, and without limitation, a smartphone, a tablet device, or a wearable device. Wireless network inputs 227 may be transmitted to wireless transceiver 208 from such wireless computing devices via any suitable wireless communication protocol, such as, and without limitation, Bluetooth®, WiFi, or wireless Internet.

In response to receiving such input, temperature controller 202 activates, deactivates, and otherwise directs thermal control apparatus associated with headphone system 100 to maintain a target temperature, or "setpoint," within a specified range, or "deadband." Such thermal control apparatus may include heating elements 204 and cooling elements 205 (shown in FIG. 2), and/or fan 531, damper 532, and/or a heat exchanger 533 (shown in FIG. 5). The value of the target temperature (setpoint) may be determined based on one or more factors, including, without limitation, a user input received via user interface 203, any of the above sensor inputs, and the current thermal control mode of headphone system 100, e.g., external condition mode, thermal transparency (internal condition) mode, target setpoint mode, user body condition mode, and temporal mode, among others. Furthermore, in some embodiments, the specific target temperature being monitored depends on the current thermal control mode of headphone system 100, as described below.

In external condition mode, temperature controller 202 determines a temperature setpoint based on a measured external temperature, such as the temperature measured by external temperature sensor 221. For example, in one embodiment, when the measured external temperature rises above a certain threshold, temperature controller 202 selects a cooler setpoint, for example as measured by acoustic cavity temperature sensor 224. Temperature controller 202 then directs thermal control apparatus associated with headphone system 100 to cool earcups 101 so that the temperature measured by acoustic cavity temperature sensor 224 remains within a specified deadband. Conversely, when the measured external temperature falls below a certain threshold, temperature controller 202 selects a warmer setpoint, as measured by acoustic cavity temperature sensor 224. Temperature controller 202 then directs thermal control apparatus associated with headphone system 100 to heat earcups 101 so that the temperature measured by acoustic cavity temperature sensor 224 remains within a specified deadband. Alternatively, temperature controller 202 may heat earcups 101 so that the temperature measured by a different temperature sensor, such as user head temperature sensor 222, remains within a specified deadband. Thus, as external temperatures rise or fall, temperature controller 202 can heat or cool earcups 101 accordingly, so that the comfort of the user is actually enhanced by wearing headphone system 100.

In thermal transparency mode, temperature controller 202 directs thermal control apparatus associated with headphone system 100 to heat or cool earcups 101 so that the temperature measured by acoustic cavity temperature sensor 224 remains within a specified deadband of the currently measured external temperature. Thus, as external temperatures rise or fall, temperature controller 202 can heat or cool earcups 101 so that headphone system 100 is substantially "thermally transparent" to the user.

In target setpoint mode, temperature controller 202 directs thermal control apparatus associated with headphone system 100 to heat or cool earcups 101 so that the temperature measured by user head temperature sensor 222, acoustic cavity temperature sensor 224, or any other predetermined temperature sensor associated with headphone system 100 remains within a specified deadband of a target setpoint temperature. For example, the target setpoint temperature may be input by the user, or determined by temperature sensor 202 based any other applicable factors, such as current heart rate or respiration rate of the user (as measured by pulse/respiration sensor 225), external temperature, type of music currently being played by loudspeaker system 201, information received via wireless network inputs 227 (such as user input from a smartphone or electronic tablet), etc.

In user body condition mode, temperature controller 202 directs thermal control apparatus associated with headphone system 100 to heat or cool earcups 101 in response to a specific temperature measured by a particular temperature sensor, such as user head temperature sensor 222, acoustic cavity temperature sensor 224, other inputs 226 (such as one or more worn body sensors), and/or any other sensor input associated with current user body condition. Thus, as the specific temperature or other sensor input increases or decreases, temperature controller 202 causes earcups 101 to cool or heat, respectively, so that the specific sensor input associated with current user body condition remains within a specified deadband of a target setpoint. For example, when the sensor input associated with current user body condition is input from user head temperature sensor 222, temperature controller 202 causes earcups 101 to cool or heat so that the temperature measured by user head temperature sensor 222 remains within a specified deadband of a target setpoint. Alternatively, temperature controller 202 causes earcups 101 to cool or heat so that the galvanic response (sweatiness) measured by galvanic skin response sensor 223 remains within a particular deadband. Any suitable algorithmic combinations of the above-described sensor inputs associated with current user body condition may also be employed in user body temperature condition mode, rather than a single sensor input.

In temporal mode, temperature controller 202 directs thermal control apparatus associated with headphone system 100 to heat or cool earcups 101 in response to temporal inputs, such as time of day and/or duration of time a user has been wearing headphone system 100. For example, in some embodiments, temperature controller 202 may include a software or firmware module configured to learn the temperature setpoint habits of a particular user with respect to time of day and/or duration of time that headphone system 100 has been worn. In such embodiments, one or both of earcups 101 may include some sort of contact sensor to determine when the user begins wearing the headphones. In some embodiments, the contact sensor may be incorporated into user head temperature sensor 222, galvanic skin response sensor 223, and/or pulse/respiration sensor 225. Furthermore, in temporal mode, temperature controller 202 may be configured to direct thermal control apparatus associated with headphone system 100 to heat or cool earcups 101 in response in any suitable temperature profile that varies with time.

By way of example, in one embodiment, 35 minutes after the user first dons headphone system 100, temperature controller 202 may direct thermal control apparatus to begin cooling earcups 101 (or acoustic cavity 210) to a specified temperature. Alternatively or additionally, temperature controller 202 may direct thermal control apparatus to cool (or heat) earcups to a specified temperature profile that varies with time. For instance, after a first time interval after the user first dons headphone system 100, temperature controller 202 may direct thermal control apparatus to begin cooling earcups 101 (or acoustic cavity 210) to a first specified temperature, then, after a second time interval, temperature controller 202 may cause cooling of earcups 101 (or acoustic cavity 210) to a second specified temperature that is lower than the first specified temperature. Alternatively or additionally, temperature controller 202 may cause cooling of earcups 101 for acoustic cavity 210) to vary incrementally from the first specified temperature to the second specified temperature.

Figure 7:
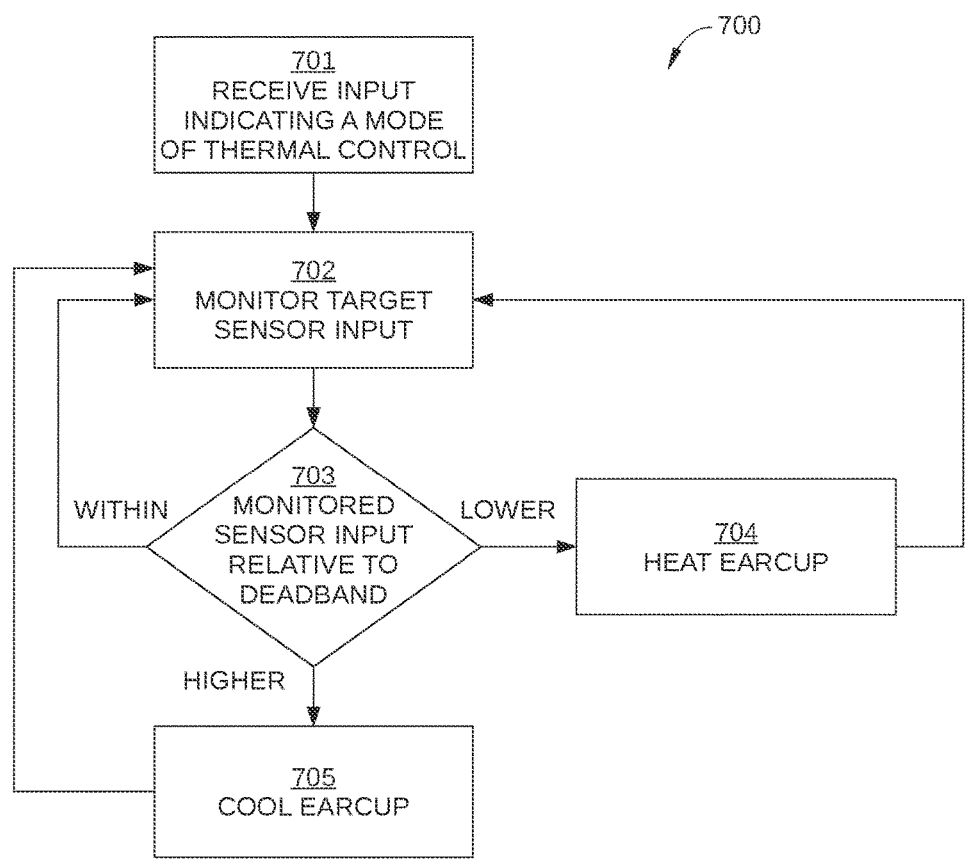
FIG. 7 sets forth a flowchart of method steps for thermally controlling a headphone system, according to the various embodiments.

FIG. 7 sets forth a flowchart of method steps for thermally controlling a headphone system, according to the various embodiments. Although the method steps are described with respect to the systems of FIGS. 1-6, persons skilled in the art will understand that any system configured to perform the method steps, in any order, falls within the scope of the various embodiments.

Prior to the method steps, temperature controller 202 may receive one or more setpoints, deadband values, or other operational parameters, either from a user or any other suitable source. For example, temperature controller 202 may receive user-specific setpoint and operational parameters via wireless network inputs 227 and/or user interface 203, as part of set-up or at any other time during normal use of headphone system 100.

As shown, a method 700 begins at step 701, in which temperature controller 202 receives an input indicating a particular mode of thermal control for headphone 100. For example, a user may select the particular mode of thermal control (e.g., external condition mode, thermal transparency mode, target setpoint mode, or user body condition mode). The mode of thermal control may be selected via user interface 203, a wireless device suitable for communication with wireless transceiver 208, or any other suitable input apparatus.

In step 702, temperature controller 202 monitors a target sensor input associated with the thermal control mode indicated in step 701. Thus, when in external condition mode, temperature controller 202 may monitor the temperature measured by external temperature sensor 221; in thermal transparency mode, temperature controller 202 may monitor the temperature measured by acoustic cavity temperature sensor 224; in target setpoint mode, temperature controller 202 may monitor the temperature measured by user head temperature sensor 222, acoustic cavity temperature sensor 224, or any other predetermined temperature sensor associated with headphone system 100; in user body condition mode, temperature controller 202 may monitor the temperature measured by any sensor input associated with current user body condition (e.g., user head temperature sensor 222, galvanic skin response sensor 223, etc.).

In step 703, temperature controller 202 determines whether the monitored sensor input is within a deadband value around the target sensor input associated with the thermal control indicated in step 701. When the monitored sensor input is within the deadband value, method 700 proceeds back to step 702; when the monitored sensor input is lower than the deadband value, method 700 proceeds to step 704 (i.e., heating); when the monitored sensor input is higher than the deadband value, method 700 proceeds to step 705 (i.e., cooling).

In step 704, performed in response to a target sensor input being lower than a deadband value, temperature controller 202 directs thermal control apparatus associated with headphone system 100 to heat earcups 101 or to increase heating of earcups 101. For example, one or more dampers 532 may be closed, fan 531 may be stopped or decreased in speed, heating output by heating elements 204 may be initiated or increased, etc. In some embodiments, temperature controller 202 may direct the thermal control apparatus to heat earcups 101 proportionate to how far below the deadband value the monitored sensor input is determined to be in step 703. Method 700 then proceeds back to step 702.

In step 705, performed in response to a target sensor input being higher than a deadband value, temperature controller 202 directs thermal control apparatus associated with headphone system 100 to cool earcups 101 or to increase cooling of earcups 101. For example, one or more dampers 532 may be opened, fan 531 may be started or increased in speed, cooling output by cooling elements 205 may be initiated or increased, etc. In some embodiments, temperature controller 202 may direct the thermal control apparatus to cool earcups 101 proportionate to how far above the deadband value the monitored sensor input is determined to be in step 703. Method 700 then proceeds back to step 702.

In some embodiments, when temperature controller 202 determines that the monitored sensor input is within the deadband value in step 702, temperature controller 202 may also perform some sort of temperature correction, rather than remaining idle until the monitored sensor input is outside a particular deadband value. Thus, in some embodiments, even when the monitored input is within the deadband value, method 700 may proceed to step 704 or 705 to adjust the monitored sensor input. For example, temperature controller 202 may employ a proportional-integral-derivative (PID), proportional-integral, proportional, or other similar control algorithm to determine how much to direct the thermal control apparatus of headphone system 100 to heat or cool earcups 101 when the monitored sensor input is determined in step 702 to be within the deadband value.

Thus, by implementation of method 700, user comfort is facilitated using any particular mode of thermal control available in headphone system 100. Consequently, headphone system 100 may be worn by a user comfortably for extended periods.

In some embodiments, headphone systems as described herein may be configured to thermally communicate with a user. For example, a headphone system may be configured to provide information or otherwise signal a user wearing the headphone system by heating and/or cooling one or both earcups of the headphone system. Thus, information or other signals may be provided to the user thermally rather than visually or aurally. One such embodiment is illustrated in FIG. 8.

Figure 8:
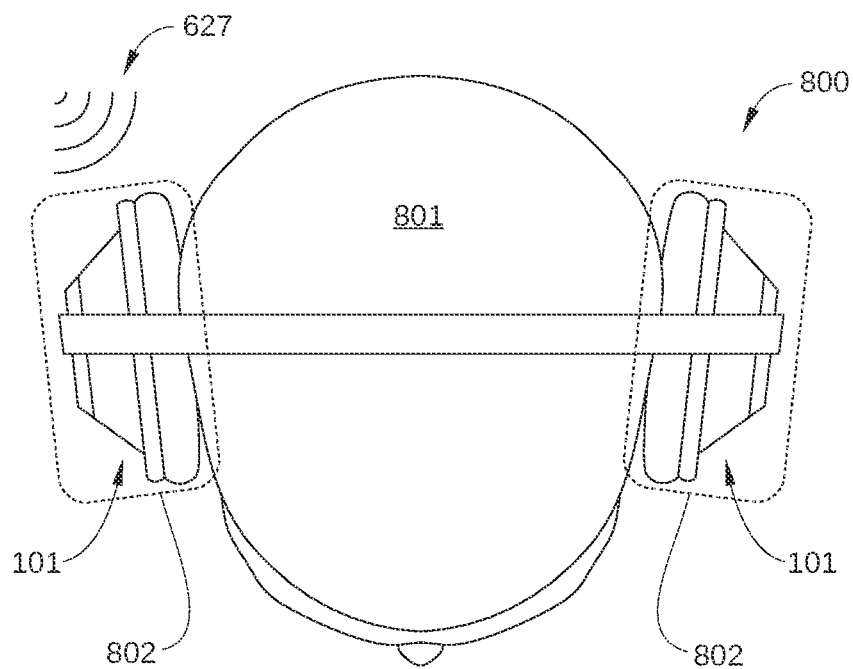
FIG. 8 schematically illustrates a user wearing a headphone system that is configured to thermally communicate with a user, according to the various embodiments.

FIG. 8 schematically illustrates a user 801 wearing a headphone system 800 that is configured to thermally communicate with a user, according to various embodiments. Headphone system 800 may be substantially similar to headphone system 100 in FIG. 1 or headphone system 400 FIG. 4. In addition, headphone system 800 is configured with a thermal communication mode, which may be used in addition to or in lieu of the thermal control modes described above. For example, via user interface 203 (shown in FIG. 2), a user may select thermal communication mode.

In thermal communication mode, one or both of earcups 101 is heated or cooled in response to a particular input received by temperature controller 202 of headphone system 800. In some embodiments, the heating and/or cooling implemented by headphone system 800 may be distinct from the comfort-related heating and cooling described above in conjunction with FIG. 6. Specifically, in some embodiments, temperature controller 202 thermally signals the user wearing headphone system 800 when a specific condition is met or signal is received. For example, as shown in FIG. 8, when a particular signal is received by headphone system 800 via wireless network inputs 227, heating or cooling 802 of earcups 101 is initiated, thereby indicating to the user that the particular signal has been received. Such a signal so received may include, without limitation, an indication that a short message service (SMS) has been received by headphone system 800 or a wireless device configured to communicate with headphone system 800 (such as a smartphone); an indication that a particular stock price has reached a predetermined value; a predetermined time period has expired or alarm time has transpired; an indication that an estimated driving time between two predetermined points has dropped below a threshold value; an indication that a particular flight has arrived; and the like.

In some embodiments, heating or cooling 802 of earcups 101 may be initiated in response to a value of a specific sensor input of headphone system 800 passing a threshold value. For example, when a heart rate and/or respiration rate of the user drops below a particular threshold, implying that the user is becoming drowsy or less attentive, headphone system 800 may initiate cooling 802 of earcups 101.

Figure 9:
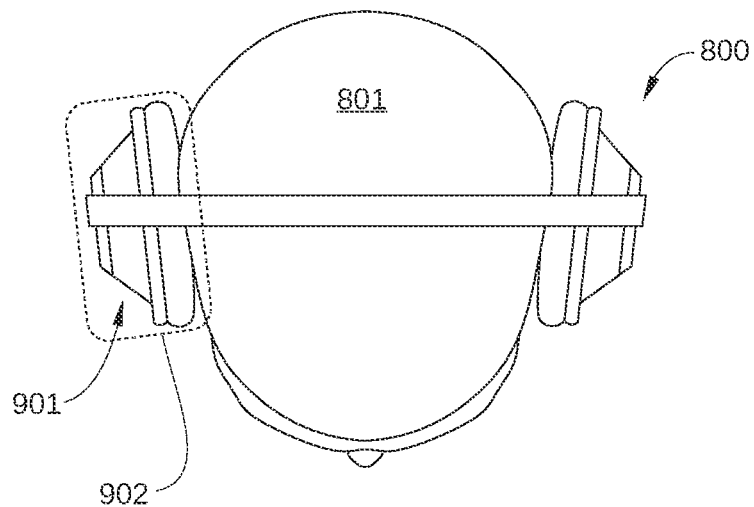
FIG. 9 schematically illustrates a user wearing a headphone system that is configured to provide thermal-based directional communications with a user, according to the various embodiments.
Figure 9:
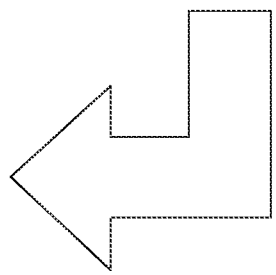

In some embodiments, heating or cooling of earcups 101 may be initiated to communicate directions to the user or to steer the attention of the user in a particular in response to a value of a specific sensor input of headphone system 800. One such embodiment is illustrated in FIG. 9. FIG. 9 schematically illustrates user 801 wearing headphone system 800 that is configured to provide thermal-based directional communications with a user, according to the various embodiments. As shown, heating or cooling 902 of a right earcup 901 is implemented to direct attention of user 801 to the right. In some embodiments, heating or cooling 802 of earcups 101 may be initiated in response to a particular person belonging to a friend network being in proximity to user 801 and/or located in particular direction from user 801. In such embodiments, heating or cooling 902 may be implemented to notify user 801 to focus his or her attention in that particular direction. Alternatively or additionally, heating or cooling 902 may be implemented to indicate a right turn, when the thermal communication from headphone system 800 is configured to provide directions or to enhance directions currently being provided aurally and/or visually (for example via a smartphone or electronic tablet) to user 801.

Figure 10:
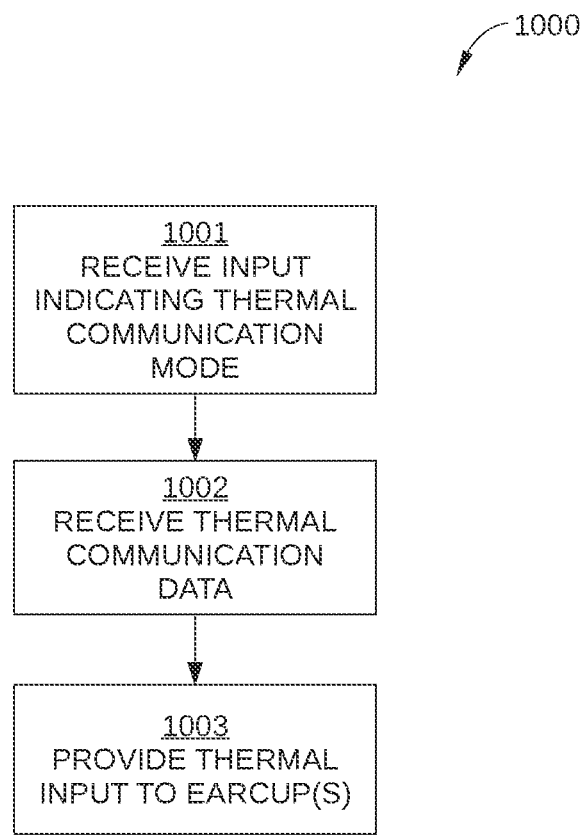
FIG. 10 sets forth a flowchart of method steps for thermally communicating with a user, according to the various embodiments.

FIG. 10 sets forth a flowchart of method steps for thermally communicating with a user, according to an embodiment. Although the method steps are described with respect to the systems of FIGS. 1-6 and 8-9, persons skilled in the art will understand that any system configured to perform the method steps, in any order, falls within the scope of the various embodiments.

As shown, a method 1000 begins at step 1001, in which headphone system 800 receives an input, either from a user or any other suitable source, indicating that headphone system 800 is in thermal communication mode. In some embodiments, the input may be received via user interface 203 and/or via a wireless device configured to communicate with headphone system 800. In some embodiments, the input may include, without limitation, one or more setpoints or other operational parameters associated with thermal communication mode. For example, user 801 may include directional information, such as a link to a GPS application, in the input. Thus, in addition to aural and/or visual directional information, user 801 may receive supplementary direction information (i.e., left or right) thermally via headphones 800. Alternatively, user 801 may include in the input an alarm time, target travel time between two particular points, or other suitable information for use as operational parameters for the thermal communication mode.

In step 1002, headphone system 800 receives thermal communication data, for example via wireless network inputs 227. For example, the thermal communication data may include instructions for headphone system 800 to indicate to user 801 to turn left or right.

In step 1003, headphone system 800 provides suitable thermal input to one or more of earcups 101. For example, a single earcup 101 may be heated or cooled when directional information is associated with the thermal communication data received in step 1002. Both earcups 101 may be heated or cooled when an alarm indicator or other binary signal is included in the thermal communication data received in step 1002.

Thus, by implementation of method 1000, user 801 receives thermal communications from headphone 800, based on sensor input or input from a remote source.

In sum, the various embodiments set forth systems and techniques for thermal control of a headphone system. By controlling a temperature based on one or more sensor inputs, the comfort of the user may be enhanced by wearing headphone system. The controlled temperature may be associated with the earcups of the headphone system or the user. Advantageously, a headphone user can comfortably wear headphones in many conditions and for an extended period without experiencing the thermal discomfort associated with wearing such headphones.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations aid/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable processors or gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

The claimed invention is:

1. An apparatus, comprising:
a first earcup coupled to a headband, wherein the first earcup includes a loudspeaker system and a thermal control subsystem;
a sensor included in the first earcup; and
a controller configured to:
detect an output generated by the sensor; and
based on the output:
transmit a first signal to at least the thermal control subsystem included in the first earcup to modify a temperature associated with at least the first earcup, and
transmit a second signal to deactivate the thermal control subsystem when the temperature reaches a threshold value.

2. The apparatus of claim 1, further comprising a second earcup coupled to the first earcup via the headband, wherein the second earcup includes a loudspeaker system and a thermal control subsystem, and wherein the controller is further configured to, based on the output, transmit a signal to at least the thermal control subsystem included in the second earcup to modify a temperature associated with at least the second earcup.

3. The apparatus of claim 1, wherein the thermal control subsystem in the first earcup includes at least one of a first air damper, a first fan, a first cooling element, and a first heating element.

4. The apparatus of claim 1, wherein the sensor comprises a sensor configured to measure a temperature external to the apparatus, a sensor configured to measure a temperature of a user wearing the apparatus, a sensor configured to measure a galvanic skin response of a user wearing the apparatus, a sensor configured to measure a temperature of an acoustic cavity of the first earcup, a sensor configured to measure a pulse rate or a respiration rate of a user wearing the apparatus, or a sensor configured to determine when a user begins wearing the apparatus.

5. The apparatus of claim 1, wherein the controller is further configured to receive an output indicating a thermal control mode associated with the apparatus.

6. The apparatus of claim 5, wherein the thermal control mode includes at least one of an external condition mode, a thermal transparency mode, a target setpoint mode, and a user body condition mode.

7. The apparatus of claim 1, wherein the thermal control subsystem included in the first earcup is coupled to a module external to the apparatus.

8. The apparatus of claim 7, wherein the external module includes at least one of a cooling system, a heating system, and a power supply.

9. The apparatus of claim 1, wherein the temperature associated with the first earcup comprises one of a temperature of a user wearing the apparatus, a temperature of an acoustic cavity of the first earcup, and a temperature of an ear-surround cushion of the first earcup.

10. The apparatus of claim 1, wherein the sensor is configured to measure a temperature external to the apparatus, and the controller is configured to transmit the signal to at least the thermal control subsystem included in the first earcup to actively control the temperature associated with the first earcup to substantially match the temperature external to the apparatus.

11. The apparatus of claim 1, wherein the output comprises a measured temperature associated with the first earcup, and the controller is configured to transmit a signal to at least the thermal control subsystem included in the first earcup to actively control the temperature associated with the first earcup to remain within a specified deadband of a target setpoint temperature.

12. The apparatus of claim 1, further comprising a second earcup coupled to the first earcup via a headband, wherein the second earcup includes a loudspeaker system and a thermal control subsystem, wherein the output comprises a sensor output associated with a body condition of a user wearing the apparatus, and wherein the controller is configured to transmit a signal to at least the thermal control subsystem included in the first earcup to modify a temperature associated with at least the second earcup to actively control the temperature associated with the first earcup to remain within a specified deadband of a target setpoint temperature.

13. A method for thermally controlling a headphone system, the method comprising:
detecting an output generated by a sensor included in a first earcup of the headphone system; and
based on the output:
transmitting a first signal to a thermal control subsystem included in the first earcup to modify a temperature associated with the first earcup, and
transmitting a second signal to deactivate the thermal control subsystem when the temperature reaches a threshold value.

14. The method of claim 13, further comprising the step of receiving a signal from a source external to the headphone system.

15. The method of claim 14, wherein the signal from the source indicates that a specific condition has been met, and further comprising transmitting a signal to at least a thermal control subsystem included in a second earcup of the headphone system to modify a temperature associated with the second earcup concurrently with transmitting the signal to at least the thermal control subsystem included in the first earcup to modify the temperature associated with at least the first earcup.

16. The method of claim 14, wherein the signal includes directional information associated with a direction relative to a user wearing the apparatus that corresponds to the first earcup.

17. A non-transitory computer readable medium storing instructions that, when executed by a processor, configure the processor to perform the steps of:

detecting an output generated by a sensor included in a first earcup of the headphone system; and based on the output:
- transmitting a first signal to at least a thermal control subsystem included in the first earcup to modify a temperature associated with at least the first earcup, and
- transmitting a second signal to deactivate the thermal control subsystem when the temperature reaches a threshold value.

18. The non-transitory computer readable medium of claim 17, further comprising the step of receiving an output indicating a thermal control mode associated with the headphone system.

19. The non-transitory computer readable medium of claim 18, wherein the thermal control mode includes at least one of an external condition mode, a thermal transparency mode, a target setpoint mode, and a user body condition mode.

20. The non-transitory computer readable medium of claim 17, wherein the temperature associated with the first earcup comprises one of a temperature of a user wearing the apparatus, a temperature of an acoustic cavity of the first earcup, and a temperature of an ear-surround cushion of the first earcup.

* * * * *

UNITED STATES PATENT AND TRADEMARK OFFICE
CERTIFICATE OF CORRECTION

PATENT NO. : 9,942,647 B2  
APPLICATION NO. : 14/874236  
DATED : April 10, 2018  
INVENTOR(S) : Davide Di Censo, Stefan Marti and Jaime Elliot Nahman Page 1 of 1

It is certified that error appears in the above-identified patent and that said Letters Patent is hereby corrected as shown below:

On the Title Page

(73) Assignee:  
Please delete "HARMAN INTERNATIONAL INDUSTRIES, INCORORATED" and insert  
--HARMAN INTERNATIONAL INDUSTRIES, INC.--.

Signed and Sealed this  
Twenty-fifth Day of June, 2019

Andrei Iancu  
*Director of the United States Patent and Trademark Office*